US005674838A

United States Patent [19]

Obermeier et al.

[11] Patent Number: 5,674,838
[45] Date of Patent: Oct. 7, 1997

[54] HIRUDIN DERIVATIVES AND A PROCESS FOR THEIR PREPARATION

[75] Inventors: Rainer Obermeier, Hattersheim; Jürgen Ludwig, Brachttal; Dominique Tripier, Eppstein; Max Hropot, Flörsheim, all of Germany

[73] Assignee: Hoechst Aktiengesellschaft, Frankfurt am Main, Germany

[21] Appl. No.: 385,551

[22] Filed: Feb. 8, 1995

[30] Foreign Application Priority Data

Feb. 10, 1994 [DE] Germany ............... 44 04 168.3

[51] Int. Cl.$^6$ .................. A61K 38/16; A61K 38/58
[52] U.S. Cl. .................. 514/8; 514/12; 530/324; 530/322
[58] Field of Search .................. 530/324, 381, 530/322; 514/12, 8

[56] References Cited

U.S. PATENT DOCUMENTS

| 4,179,337 | 12/1979 | Davis et al. ............ 435/181 |
| 4,791,100 | 12/1988 | Kramer et al. .......... 514/12 |
| 4,847,325 | 7/1989 | Shadle et al. .......... 525/54.1 |
| 5,087,613 | 2/1992 | Courtney et al. ....... 514/12 |
| 5,180,668 | 1/1993 | Crause et al. .......... 435/69.2 |
| 5,362,858 | 11/1994 | Bischoff ............... 530/410 |
| 5,458,568 | 10/1995 | Racchini et al. ....... 604/19 |

FOREIGN PATENT DOCUMENTS

| 614121 | 11/1989 | Australia . |
| 2067224 | 6/1991 | Canada . |
| 0056951B1 | 8/1982 | European Pat. Off. . |
| 0142860A2 | 5/1985 | European Pat. Off. . |
| 0158564B1 | 10/1985 | European Pat. Off. . |
| 0158986B1 | 10/1985 | European Pat. Off. . |
| 0168342B1 | 1/1986 | European Pat. Off. . |
| 0171024B1 | 2/1986 | European Pat. Off. . |
| 0193175A2 | 9/1986 | European Pat. Off. . |
| 0209061B1 | 1/1987 | European Pat. Off. . |
| 0227938B1 | 7/1987 | European Pat. Off. . |
| 0316650B1 | 5/1989 | European Pat. Off. . |
| 0324712B1 | 7/1989 | European Pat. Off. . |
| 0-332523 | 9/1989 | European Pat. Off. . |
| 0-341215 | 11/1989 | European Pat. Off. . |
| 0345616A2 | 12/1989 | European Pat. Off. . |
| 0-557199 | 8/1993 | European Pat. Off. . |
| 3445517C2 | 6/1986 | Germany . |
| 4224213A1 | 1/1993 | Germany . |
| WO-A-9108229 | 6/1991 | WIPO . |
| WO 92/01712 | 2/1992 | WIPO . |

OTHER PUBLICATIONS

Zawilska et al., "The Effect of a Long–Acting Recombinant Hirudin (PEG–Hirudin) on Experimental Disseminated Intravascular Coagulation (DIC) in Rabbits," Thrombosis Research 69, 1993, pp. 315–320.

European Search Report App. No. EP 95 101 554.4 dated Jun. 22, 1995 and Annex thereto.

Jürgens, J., "Über das Verhalten antithrombischer Substanzen bei Erkrankungen der Leber," Deutsches Archiv. für Klinische Medizin, Bd. 200, S. 67–85 (1952).

Walsmann, P., and F. Markwardt, "Biochemische und Pharmakologische Aspekte des Thrombininhibitors Hirudin," Pharmazie, 36(10):653–660(1981).

Chang, J.-Y., "The functional domain of hirudin, a thrombin-specific inhibitor," FEBS, 164(2):307–313 (1983).

Jakubke, H.-D., "Enzymatic Peptides Synthesis," The Peptides, vol. 9, Chap. 3, pp. 103–165 (The Academic Press, Inc., 1987).

Tripier, D., "Hirudin: A Family of Iso–Proteins—Isolation and Sequence Determination of New Hirudins," Folia Haematol., Leipzig 115, 1–2, S. 30–35 (1988).

Rudinger T. (1976) Peptide Hormones, (ed T. Parsons), University Park Press, Baltimore, pp. 1–7.

Primary Examiner—Cecilia J. Tsang
Assistant Examiner—Anish Gupta
Attorney, Agent, or Firm—Finnegan, Henderson, Farabow, Garrett & Dunner, L.L.P.

[57] ABSTRACT

Hirudin derivatives can be prepared by the selective enzymic replacement of a part of the molecule with an amino derivative. The hirudin derivatives are suitable for preparing pharmaceuticals having an anticoagulatory effect.

16 Claims, No Drawings

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 65 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: desulfato-Tyr63 hirudin (ix) FEATURE:
    (A) NAME/KEY: protein
    (B) LOCATION: 1..65

(xi) SEQUENCE DESCRIPTION: SEQ ID NO:1:

| Leu | Thr | Tyr | Thr | Asp | Cys | Thr | Glu | Ser | Gly | Gln | Asn | Leu | Cys | Leu | Cys |
|---|---|---|---|---|---|---|---|---|---|---|---|---|---|---|---|
| 1 | | | | 5 | | | | | 10 | | | | | 15 | |
| Glu | Gly | Ser | Asn | Val | Cys | Gly | Gln | Gly | Asn | Lys | Cys | Ile | Leu | Gly | Ser |
| | | | 20 | | | | 25 | | | | | 30 | | | |
| Asp | Gly | Glu | Lys | Asn | Gln | Cys | Val | Thr | Gly | Glu | Gly | Thr | Pro | Lys | Pro |
| | | 35 | | | | | 40 | | | | | 45 | | | |
| Gln | Ser | His | Asn | Asp | Gly | Asp | Phe | Glu | Glu | Ile | Pro | Glu | Glu | Tyr | Leu |
| | 50 | | | | | 55 | | | | | 60 | | | | |
| Gln | | | | | | | | | | | | | | | |
| 65 | | | | | | | | | | | | | | | |

(2) INFORMATION FOR SEQ ID NO:2:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: hirudin derivative (ix) FEATURE:
        (A) NAME/KEY: protein
        (B) LOCATION: 1..64

(xi) SEQUENCE DESCRIPTION: SEQ ID NO:2:

| Leu | Thr | Tyr | Thr | Asp | Cys | Thr | Glu | Ser | Gly | Gln | Asn | Leu | Cys | Leu | Cys |
|---|---|---|---|---|---|---|---|---|---|---|---|---|---|---|---|
| 1 | | | | 5 | | | | | 10 | | | | | 15 | |
| Glu | Gly | Ser | Asn | Val | Cys | Gly | Gln | Gly | Asn | Lys | Cys | Ile | Leu | Gly | Ser |
| | | | 20 | | | | 25 | | | | | 30 | | | |
| Asp | Gly | Glu | Lys | Asn | Gln | Cys | Val | Thr | Gly | Glu | Gly | Thr | Pro | Lys | Pro |
| | | 35 | | | | | 40 | | | | | 45 | | | |
| Gln | Ser | His | Asn | Asp | Gly | Asp | Phe | Glu | Glu | Ile | Pro | Glu | Glu | Tyr | Thr |
| | 50 | | | | | 55 | | | | | 60 | | | | |

(2) INFORMATION FOR SEQ ID NO:3:

(i) SEQUENCE CHARACTERISTICS:
        (A) LENGTH: 66 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: hirudin derivative (ix) FEATURE:
        (A) NAME/KEY: protein
        (B) LOCATION: 1..66

(xi) SEQUENCE DESCRIPTION: SEQ ID NO:3:

| Leu | Thr | Tyr | Thr | Asp | Cys | Thr | Glu | Ser | Gly | Gln | Asn | Leu | Cys | Leu | Cys |
|---|---|---|---|---|---|---|---|---|---|---|---|---|---|---|---|
| 1 | | | | 5 | | | | | 10 | | | | | 15 | |
| Glu | Gly | Ser | Asn | Val | Cys | Glu | Gln | Gly | Asn | Lys | Cys | Ile | Leu | Gly | Ser |
| | | | 20 | | | | 25 | | | | | 30 | | | |

```
Asp Gly Glu Lys Asn Gln Cys Val Thr Gly Glu Gly Thr Pro Lys Pro
         35                  40                 45
Gln Ser His Asn Asp Gly Asp Phe Glu Glu Ile Pro Glu Glu Tyr Thr
         50                  55                 60
Arg Arg
65
```

( 2 ) INFORMATION FOR SEQ ID NO:4:

( i ) SEQUENCE CHARACTERISTICS:
    ( A ) LENGTH: 37 amino acids
    ( B ) TYPE: amino acid
    ( C ) STRANDEDNESS: single
    ( D ) TOPOLOGY: linear ( i i ) MOLECULE TYPE: protein ( i x ) FEATURE:
    ( A ) NAME/KEY: protein
    ( B ) LOCATION: 1..37

( x i ) SEQUENCE DESCRIPTION: SEQ ID NO:4:

```
Leu Thr Tyr Thr Asp Cys Thr Glu Ser Gly Gln Asn Leu Cys Leu Cys
1                 5                  10                 15
Glu Gly Ser Asn Val Cys Gly Gln Gly Asn Lys Cys Ile Leu Gly Ser
         20                  25                 30
Asp Gly Glu Lys Thr
         35
```

( 2 ) INFORMATION FOR SEQ ID NO:5:

( i ) SEQUENCE CHARACTERISTICS:
    ( A ) LENGTH: 29 amino acids
    ( B ) TYPE: amino acid
    ( C ) STRANDEDNESS: single
    ( D ) TOPOLOGY: linear ( i i ) MOLECULE TYPE: protein ( i x ) FEATURE:
    ( A ) NAME/KEY: protein
    ( B ) LOCATION: 1..29

( x i ) SEQUENCE DESCRIPTION: SEQ ID NO:5:

```
Asn Gln Cys Val Thr Gly Glu Gly Thr Pro Lys Pro Gln Ser His Asn
1                 5                  10                 15
Asp Gly Asp Phe Glu Glu Ile Pro Glu Glu Tyr Leu Gln
         20                  25
```

( 2 ) INFORMATION FOR SEQ ID NO:6:

( i ) SEQUENCE CHARACTERISTICS:
    ( A ) LENGTH: 64 amino acids
    ( B ) TYPE: amino acid
    ( C ) STRANDEDNESS: single
    ( D ) TOPOLOGY: linear ( i i ) MOLECULE TYPE: protein ( v i ) ORIGINAL SOURCE:
    ( A ) ORGANISM: hirudin derivative ( i x ) FEATURE:
    ( A ) NAME/KEY: protein
    ( B ) LOCATION: 1..64

( x i ) SEQUENCE DESCRIPTION: SEQ ID NO:6:

```
Leu Thr Tyr Thr Asp Cys Thr Glu Ser Gly Gln Asn Leu Cys Leu Cys
```

5,674,838

-continued

```
           1               5                        10                        15
       Glu Gly Ser Asn Val Cys Gly Gln Gly Asn Lys Cys Ile Leu Gly Ser
                   20                      25                    30

Asp Gly Glu Lys Asn Gln Cys Val Thr Gly Glu Gly Thr Pro Lys Pro
                   35                      40                    45

Gln Ser His Asn Asp Gly Asp Phe Glu Glu Ile Pro Glu Glu Tyr Xaa
                   50                      55                    60
```

( 2 ) INFORMATION FOR SEQ ID NO:7:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: protein
        ( B ) LOCATION: 1..37

( x i ) SEQUENCE DESCRIPTION: SEQ ID NO:7:

```
       Leu Thr Tyr Thr Asp Cys Thr Glu Ser Gly Gln Asn Leu Cys Leu Cys
       1               5                       10                    15

Glu Gly Ser Asn Val Cys Gly Gln Gly Asn Lys Cys Ile Leu Gly Ser
                   20                      25                    30

Asp Gly Glu Lys Xaa
                   35
```

( 2 ) INFORMATION FOR SEQ ID NO:8:

( i ) SEQUENCE CHARACTERISTICS:
        ( A ) LENGTH: 64 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: hirudin derivative ( i x ) FEATURE:
        ( A ) NAME/KEY: protein
        ( B ) LOCATION: 1..64

( x i ) SEQUENCE DESCRIPTION: SEQ ID NO:8:

```
       Leu Thr Tyr Thr Asp Cys Thr Glu Ser Gly Gln Asn Leu Cys Leu Cys
       1               5                       10                    15

Glu Gly Ser Asn Val Cys Gly Gln Gly Asn Lys Cys Ile Leu Gly Ser
                   20                      25                    30

Asp Gly Glu Lys Asn Gln Cys Val Thr Gly Glu Gly Thr Pro Lys Pro
                   35                      40                    45

Gln Ser His Asn Asp Gly Asp Phe Glu Glu Ile Pro Glu Glu Tyr Xaa
                   50                      55                    60
```

HIRUDIN DERIVATIVES AND A PROCESS FOR THEIR PREPARATION

The invention relates to hirudin derivatives, to their preparation by the selective enzymic replacement of a part of the molecule by an amine derivative, and to the use of the hirudin derivatives as pharmaceuticals.

Hirudin is a protein which is composed of 65 amino acid residues and which can be isolated from the salivary glands of the leech (Hirudo medicinalis). As a selective inhibitor of thrombin, it has a coagulation-inhibiting effect (Pharmazie 36, 633–660 (1981). The single-chain polypeptide possesses three disulfide bridges which stabilize the domain between the amino acids in positions 1 to 49 as a strongly folded, compact protein tertiary structure. Linearized, the C-terminal amino acid sequence 55 to 65 represents the anchor sequence for binding to thrombin. Native hirudin carries a sulfate radical on the phenolic OH group of the tyrosine residue in position 63, thereby strengthening the acidic character of this region of the sequence, which character is already caused by clusters of acidic amino acid residues. Eliminating the sulfate group increases the value of the dissociation constant, $K_D$, which is given for the hirudin/thrombin interaction in a range from 60 pmol–20 fmol.

Chemically and enzymically prepared derivatives of hirudin can be found in EP 0 493 588 (nitro group, halogen substitution) and DE 4 224 213 (C-terminal, enzymic amidation). Conjugates of free amino groups of the N-terminus or the lysyl side chains with saccharides or polyethylene glycol (PEG) are demonstrated in U.S. Pat. No. 4,179,337 and U.S. Pat. No. 4,847,325.

For use as long-acting pharmaceuticals, conventional polyethylene glycol derivatives of hirudin are prepared by chemically coupling a functional group of an amino acid contained in the hirudin with a polyethylene glycol residue (PEG) (cf. EP 0 345 616). Under these circumstances, no defined compounds are produced since, as a rule, the residue can be bonded at several functional sites in the hirudin molecule.

Hirudin contains the amino acids lysine, tyrosine and phenylalanine at three, two and one position(s), respectively, in the molecule. Such sites in a protein are usually cleaved by serine proteases such as trypsin or chymotrypsin. Previously known enzymic semisynthetic methods (The Peptides, S. Udenfriend and J. Meienhofer (Eds.), Vol. 9, Acad. Press, NY, 1987, 103–165) did not therefore appear to be applicable to hirudin. On the basis of specialist knowledge, it is to be expected that inactive degradation products of hirudin would be formed preferentially.

It has been found that, under certain reaction conditions, a selective transpeptidation, leading to novel compounds, takes place in enzymic semisynthetic reactions of hirudin with chymotrypsin, trypsin or a comparable enzyme (e.g. lysyl endopeptidase).

The invention relates to compounds of the formula I or II:

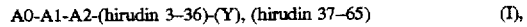

where Y is an amine derivative,

A1 and A2 are, independently of each other, an amino acid residue, and

A0 is an amino acid residue or a hydrogen atom.

The nomenclature used in formulae I and II refers to the publication by D. Tripier in Folia Haematol. (Leipzig) 115, 30–35 (1988).

The comma in formula I denotes that the amino acid sequence of the underlying hirudin is interrupted between positions 36 and 37 and that the compound contains two hirudin fragments which are connected by way of disulfide bridges. The amine derivative Y is linked by an amide bond to the amino acid in position 36 of the original sequence of the underlying hirudin.

Formula II shows a compound which contains an amine derivative Y which is linked by an amide bond to the amino acid in position 63 of the original sequence of the underlying hirudin.

Amine derivatives Y are preferably compounds of the formula IIIa or IIIb:

where:

A is a) an amino acid residue, or b) a peptide having from 2 to 10 amino acid residues, R is a) $(C_1-C_{10})$-alkyl, branched or straight-chain, or b) $(C_1-C_{10})$-alkyl, branched or straight-chain, substituted once or more than once, independently of each other, by
 1) phenyl,
 2) indolyl,
 3) imidazolyl, or
 4) phenyl, substituted once or more than once by hydroxyl, c) phenyl, or d) naphthyl, $R^1$ is a) a hydrogen atom, b) a covalent bond, c) a sugar such as glucose, fructose, mannose, galactose, ribose, ribulose or xylose, d) a polysaccharide containing from 2 to 10 sugars, or e) $-[O-(CH_2)_m]_n-$, where:
 m is an integer 2, 3, 4 or 5, and
 n is an integer from 1 to 100, and X is a) a hydrogen atom, b) $-OR^2$, c) $-SR^2$, d) $-NHR^2$, e) $-COOR^2$, or f) A, where:

$R^2$ is 1) a hydrogen atom,

2) $(C_1-C_{10})$-alkyl, branched or straight-chain,

3) $(C_1-C_{10})$-alkyl, branched or straight-chain, substituted once or more than once by
 3.1 phenyl,
 3.2 indolyl,
 3.3 imidazolyl, or
 3.4 phenyl, substituted once or more than once by hydroxyl, 4) phenyl, or 5) naphthyl.

Amine derivatives Y of the formula IIIa or IIIB are preferred in which:

A is a peptide having from 2 to 5 amino acid residues,

R is ethyl, substituted by
1) phenyl,
2) indolyl,
3) imidazolyl, or
4) 4-hydroxyphenyl, $R^1$ is $-[O-(CH_2)_m]_n-$, in which:
 m is the number 2, and
 n is an integer from 20 to 50, X is
 a) a hydrogen atom,
 b) $-OR^2$,
 c) $-NHR^2$, or
 d) $-COOR^2$,
 in which:
  $R^2$ is
  1) a hydrogen atom,
  2) $(C_1-C_5)$-alkyl, or
  3) phenyl.

Amine derivatives Y of the formula IIIa or IIIb are especially preferred in which:

A is a peptide having from 2 to 5 amino acid residues from the group Thr or Arg, $R^1$ is
 a) a hydrogen atom,
 b) a covalent bond,
 c) glucose, or
 d) polyethylene glycol having a molecular weight of from 100 to 3000 g/mol, X is
 a) a hydrogen atom, or
 b) $-OR^2$, where $R^2$ is tertiary butyl.

$-[O-(CH_2)_m]_n-$ radicals having a molecular weight of 1500 g/mol are especially preferred.

An amino acid is understood to mean a natural, a genetically encodable, unnatural, non-encodable, L- or D-amino acid.

Examples of an L- or D-amino acid are: alanine, valine, leucine, isoleucine, serine, threonine, cysteine, cystine, methionine, ornithine, citrulline, arginine, lysine, asparagine, aspartic acid, glutamic acid, glutamine, phenylalanine, tyrosine, thyroxine, proline, hydroxyproline, tryptophan and histidine. Glycine and gamma-aminobutyric acid are further examples of an amino acid.

The invention also relates to a process for preparing compounds of the formula I and II wherein amine derivatives and hirudin are reacted in the presence of proteases, preferably serine proteases, preferably chymotrypsin, trypsin, trypsin, trypsin-like enzymes or lysyl endopeptidase.

Examples of hirudins which can be employed are those disclosed in the following: EP 142 860, EP 158 564, EP 158 986, EP 168 342, EP 171 024, EP 193 175, EP 209 061, EP 227 938, DE 34 45 517, DE 38 05 540.6; Chang, FEBS 164, 307 (1983); Tripier (Folia Haematol. (Leipzig) 115, 30–35 (1988). Sequence listing ID NO: 1 shows an example of the structure of a hirudin.

Examples of suitable hirudins are the compounds described in the above-cited references, in particular the compounds described in EP 171 024, EP 158 986, EP 209 061 and DE 38 05 540.6, e.g.:

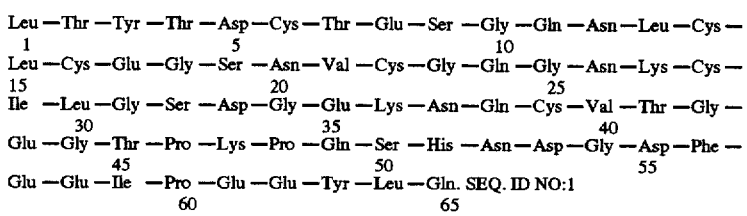

These hirudins my be prepared by methods of peptide chemistry which are well known to the person skilled in the art or by equivalent known methods. Alternatively, the hirudins mentioned can be obtained by recombinant DNA methods which are known to the person skilled in the art.

Compounds of the formula I are formed from a hirudin and an excess of a suitable amine derivative of the formulae IIIa or IIIb using trypsin or a trypsin-like enzyme, e.g. lysyl endopeptidase. Suitable amine derivatives are those which, if trypsin is used, do not carry any free (i.e. any unprotected) arginyl side chain or lysyl side chain, or, if lysyl endopeptidase is used, do not carry any free lysyl side chain. Transpeptidation takes place at the C terminus of the lysine residue in position 36 of the amino acid sequence of the hirudin employed. In this reaction, the peptide bond Lys-Asn- (36–37) is opened and the amine derivative is bonded unambiguously to the carboxyl group of the Lys residue. This results in a "two-chain" hirudin derivative which is held together by three disulfide bridges. Thus, two terminal amino acid residues A0, or A1 if A0 is dispensed with, and Asn37 (asparagin in position 37 of the underlying hirudin amino acid sequence) can be detected by N-terminal amino acid sequence analysis (Edman degradation), thereby confirming that the hirudin derivative has a two-chain structure.

Compounds of the formula II are formed from a hirudin and an excess of a suitable amine derivative of the formulae IIIa or IIIb using chymotrypsin or an enzyme which acts in a comparable manner. In this case, suitable amine derivatives are those which do not carry any free tyrosyl side chain. A transpeptidation takes place at the C terminus of the tyrosine residue in position 63 of the amino acid sequence of the hirudin employed. In this reaction, the dipeptide composed of the amino acids at positions 64 and 65 of the amino acid sequence of the underlying hirudin is replaced by an amine derivative.

The amine derivative is employed in excess. Preferably, there is a 50- to 150-fold molar excess of the amine derivative in relation to the quantity of hirudin. The amine derivative is preferably employed in as high a concentration as possible. Water, or a mixture of water and a nonprotonating organic solvent, such as dimethylformamide, serve as the solvent. The mixture preferably contains less than 25% by volume (v/v) of water. The use of organic solvents which are miscible with water is advantageous in the case of amine derivatives which are sparingly soluble in water. In this way, the reaction mixture can be rendered homogeneous. The quantity of enzyme preferably corresponds to from 5 to 10% by weight of the quantity of hirudin employed. The reaction is preferably carried out at a pH of from 4 to 6 and at a reaction temperature of from 0° C. to 40° C., particularly preferably at a temperature of from 0° to 10°C.

The enzymes which are used can be of differing biological provenance, for example trypsin can be of porcine or bovine origin.

When amino acid esters or oligopeptide esters are used as the amine derivative, the enzyme-catalyzed conversion of hirudin results in the corresponding hirudin derivative esters. If desired, the ester groups can be eliminated by customary methods. However, it is advantageous only to eliminate the ester groups of the intermediates after chromatographic purification has taken place.

The enzyme-catalyzed semisynthesis of hirudin derivatives according to the invention is a process which complements recombinant processes for altering the hirudin structure. In particular, non-encodable amino acids, such as D-amino acids, or any arbitrary amine derivatives can be introduced in a specific manner using the semisynthesis.

The process to which the invention relates makes it possible, for example, to prepare a defined hirudin/ polyethylene glycol derivative of the formula I or II, which can be used medically as a slow-release preparation. A polyethylene glycol which is esterified with an amino acid or an oligopeptide can, as the amine derivative, be reacted very selectively with a hirudin so that the polyethylene glycol residue is only bonded once at a defined position.

Other hirudin derivatives prepared in accordance with the invention can be of therapeutic value for transdermal administration, e.g. iontophoresis. The administration of hirudin derivatives by iontophoresis is an additional subject of the invention.

The invention also relates to pharmaceuticals which contain an effective quantity of at least one compound of the formula I and/or II.

The invention furthermore relates to the use of the compounds of the formula I and II as pharmaceuticals having an anticoagulatory effect.

The following examples, in which recombinantly obtained desulfato-Tyr63 hirudin (sequence listing ID NO: 1) is used, are intended to elucidate the invention without, however, limiting it to these examples.

EXAMPLE 1

Preparation of Hirudin

Hirudin is synthesized, for example, in yeast cells which secrete hirudin in accordance with EP 0324712. Hirudin is then enriched chromatographically on a column containing ®Diaion HP20 (Mitsubishi Chem. Ind., Japan) (see EP 0316650). Following dialysis and subsequent affinity chromatography on thrombin-Sepharose, final purification is effected by reversed-phase HPLC.

EXAMPLE 2

3 g of recombinantly obtained desulfato-Tyr63 hirudin (sequence listing SEQ ID NO: 1) are dissolved, together with 20 g of Thr(But)OBut acetate (threonine provided with tert-butyl protective groups; for preparation, see EP 0056951) in 6 ml of water, and 190 mg of chymotrypsin (Merck, Darmstadt) are added to this solution. The pH of the solution is adjusted to 4.5 and the reaction mixture is stored at 4° C. for 72 hours.

After that, the reaction mixture is diluted with 100 ml of methanol, and 300 ml of dimethyl ether are added. The precipitate which is obtained is centrifuged down. The residue is washed once again with a mixture of methanol/ diethyl ether (1:2 v/v), washed with ether when centrifuged down and dried under reduced pressure. Yield: 3.6 g of crude product.

The crude product is composed of unreacted hirudin, the desired hirudin derivative and by-products which have arisen as a result of enzymic cleavage. Analysis of the crude product by analytical HPLC showed: 39.6% (hirudin 1–63) -Thr(But)OBut(64), 45.9% (hirudin 1–65) and 6.3% cleavage products.

The crude product is separated chromatographically on a preparative HPLC column (5×25 cm, stationary phase is a reverse-phase $C_{18}$ material) by gradient elution using acetonitrile/water/trifluoroacetic acid. Owing to its lipophilic tert-butyl protective groups, (hirudin 1–63)-Thr(But) OBut elutes with a markedly delayed retention time. The fraction containing the pure intermediate is collected, the acetonitrile is evaporated off under reduced pressure and the aqueous solution is freeze-dried.

Yield: 963 mg of (hirudin-63)-Thr(But)OBut(64) (purity: 93.6%).

The hirudin derivative which has been obtained is dissolved in 20 ml of 95% trifluoroacetic acid and this solution is kept at room temperature for 45 minutes. After that, 100 ml of ice-cooled dimethyl ether are added to it. The precipitate which is obtained is centrifuged down, washed a further three times with ether, and then dried under reduced pressure.

Yield: 802 mg of (hirudin-63)-Thr64 (see sequence listing SEQ ID NO: 2).

Amino acid analysis of the product conforms with the composition which is to be expected from the amino acid sequence.

EXAMPLE 3

3 g of recombinantly obtained desulfato-Tyr63 hirudin (sequence listing ID NO: 1) are reacted, as in Example 2, with 41 g of Thr(But)-Arg-Arg (synthesized by standard methods) and 170 mg of chymotrypsin (Merck, Darmstadt).

Once the reaction is complete, 300 ml of methanol and 150 ml of dimethyl ether are added to the mixture. The precipitate which is centrifuged down is washed three times with methanol/ether and then with ether and dried in vacuo. Yield: 4.8 g of crude product. Analytical HPLC (stationary phase $C_{18}$ silica gel, eluent acetonitrile/$H_2O$/trifluoroacetic acid) shows the following composition: 65.2% (hirudin 1–63)-Thr(But) (64)-Arg(65)-Arg(66)-OH; 3.9% (hirudin-65); 18.7% cleavage products. Chromatographic purification and isolation of the product are carried out as in Example 2.

Yield: 1.55 g of (hirudin 1–63)-Thr(But) (64)-Arg(65)- Arg(66)—OH; Purity: 90.3%.

The tert-butyl protective group on the threonine side chain is eliminated in a known manner as in Example 2. Yield: 1.2 g of (hirudin 1–63)-Thr(64)-Arg(65)-Arg(66)—OH (see sequence listing SEQ ID NO: 3).

Amino acid analysis of the product conforms with the composition which is to be expected from the amino acid sequence.

When its anticoagulatory effect is determined following intravenous administration to Rhesus monkeys (1 mg/kg), this hirudin derivative exhibits, despite changes in its isoelectric point, an activity which is virtually identical to that of the starting hirudin (test conditions, see: J. Jürgens, Dtsch. Arch. Klin. Med. 200, 67 (1952)).

EXAMPLE 4

3 g of recombinantly obtained desulfato-Tyr63 hirudin (sequence listing SEQ ID NO: 1) are reacted, as in Example 2, with 20 g of Thr(But)OBut acetate and 200 mg of trypsin (Merck, Darmstadt).

The reaction is terminated after 72 hours and working-up is carried out as in Example 2. Yield: 4.2 g of crude product having the following composition: 554 (hirudin 1–36)-Thr (But)OBut, (hirudin 37–65); 31% unreacted hirudin; 15% cleavage products. Chromatographic purification and subsequent isolation are carried out as in Example 2. Yield: 1.65 g of (hirudin 1–36)-Thr(But)OBut, (hirudin 37–65).

The tert-butyl protective groups of the threonine residue are eliminated as in Example 2. Yield: 1.3 g of (hirudin 1–36)-Thr, (hirudin 37–65). The structure of the first chain of the hirudin derivative, (hirudin 1–36)-Thr, is given by SEQ ID NO: 4, and the structure of the second chain of the hirudin derivative, (hirudin 37–65), by sequence listing SEQ ID NO: 5.

Amino acid analysis of the product conforms with the composition which is to be expected from the amino acid sequence. Edman sequence analysis indicates 2 N-terminal amino acid residues Leu(1) and Asn(37). When its anticoagulatory effect is determined following intravenous administration to Rhesus monkeys, this hirudin derivative surprisingly exhibits, despite substantial structural alterations, an activity which is virtually identical to that of the starting hirudin.

EXAMPLE 5

H.Thr-O-PEG$_{1500}$ is prepared, in accordance with known methods of peptide chemistry, by reacting polyethylene glycol monomethyl ether and tert-butoxycarbonyl-threonine, for example in a one-pot reaction using hydroxybenzotriazole and dicyclohexylcarbodiimide.

3 g of recombinantly obtained desulfato-Tyr63 hirudin (sequence listing SEQ ID NO: 1) are reacted with 80 g of H.Thr-O-PEG$_{1500}$, as in Example 2, together with 250 mg of chymotrypsin. 35 ml of dimethylformamide, as a solubilizing agent, are also added to the reaction mixture.

Once the reaction is complete, the reaction mixture is diluted with 200 ml of methanol, and unreacted hirudin, as well as PEG-hirudin, are precipitated by adding dimethyl ether.

The crude product, which is centrifuged down, is washed three times with a mixture comprising methanol/ether (2:1, V/V) and dried under reduced pressure. PEG-hirudin and hirudin can be separated, as in Example 2, by means of preparative HPLC or, better, by means of chromatographic purification on a cation exchange column (Fractogel-EMD-SO$_3$; Merck, Darmstadt). Yield: 1.9 g of (hirudin 1–63)-Thr-O-PEG, see sequence listing SEQ ID NO: 6.

Amino acid analysis of the product conforms with the composition which is to be expected from the amino acid sequence.

The presence of the PEG conjugation is demonstrated by chymotryptic digestion in dilute aqueous solution and subsequently using thin layer chromatography to make a comparison with Thr-O-PEG and free threonine. When this is done, no free threonine can be detected within the analytical limits.

EXAMPLE 6

3 g of the recombinantly obtained desulfato-Tyr63 hirudin (sequence listing ID NO: 1) are dissolved in 6 ml of water with 25 g of D-Glu(OBut)$_2$ acetate (Sigma, Deisenhofen) 0 and 190 mg of trypsin are added to this solution. The pH of the solution is adjusted to 4.5 and the reaction mixture is stored at 4° C. for 72 hours.

The further procedure, and the working-up, are carried out in analogy with Example 2. For the structure of the product composed of two peptide chains, see the sequence listings of the constituent sequences, SEQ ID NO: 7 and SEQ ID NO: 5.

EXAMPLE 7

3 g of the recombinantly obtained desulfato-Tyr63 hirudin (sequence listing ID NO: 1) are dissolved in 6 ml of water together with 30 g of D-Glu(O)But)$_2$ acetate (Sigma, Deisenhofen), and 190 mg of chymotrypsin are added to this solution. The pH of the solution is adjusted to 4.5 and the reaction mixture is stored at 4° C. for 72 hours. The further procedure, and the working-up, are carried out in analogy with Example 2.

The structure of the product comprises one chain (sequence listing SEQ ID NO: 8).

---

We claim:

1. A compound of the formula I or II,

A0-A1-A2-(hirudin 3–36)-(Y), (hirudin 37–65)    (I),

A0-A1-A2-(hirudin 3–63)-(Y)    (II),

A1 is an amino acid residue,
A2 is an amino acid residue,
A0 is an amino acid residue or a hydrogen atom,
Y is an amine derivative of the formula IIIa or IIIb:

NH—R—X    (IIIa),

A—R$^1$—X    (IIIb), where:
A is a) a peptide having from 2 to 5 amino acid residues, wherein a residue is selected from the group consisting of Thr and Arg.

R is
a) $(C_1-C_{10})$-alkyl, branched or straight-chain, or
b) $(C_1-C_{10})$-alkyl, branched or straight-chain, substituted once or more than once, independently of each other, by
 1) phenyl,
 2) indolyl,
 3) imidazolyl, or
 4) phenyl, substituted once or more than once by hydroxyl,
c) phenyl, or
d) naphthyl, $R^1$ is
a) a hydrogen atom,
b) a covalent bond,
c) a monosaccharide xylose,
d) a polysaccharide containing from 2 to 10 monosaccharides, or
e) $-[O-(CH_2)_m]_n-$, where:
 m is an integer 2, 3, 4 or 5, and
 n is an integer from 1 to 100, and X is
a) a hydrogen atom,
b) $-OR^2$,
c) $-SR^2$,
d) $-NHR^2$,
e) $-COOR^2$, or
f) A,
where:
 $R^2$ is
  1) a hydrogen atom,
  2) $(C_1-C_{10})$-alkyl, branched or straight-chain,
  3) $(C_1-C_{10})$-alkyl, branched or straight-chain, substituted once or more than once by
   3.1 phenyl,
   3.2 indolyl,
   3.3 imidazolyl, or
   3.4 phenyl, substituted once or more than once by hydroxyl,
  4) phenyl, or
  5) naphthyl.

2. A compound of the formula I or II as claimed in claim 1, in which:
R is ethyl, substituted by
 1) phenyl,
 2) indolyl,
 3) imidazolyl, or
 4) 4-hydroxphenyl,
$R^1$ is $-[O-(CH_2)_m]_n-$, in which:
 m is the number 2, and
 n is an integer from 20 to 50,
X is
 a) hydrogen atom,
 b) $-OR^2$,
 c) $-NHR^2$, or
 d) $-COOR^2$,
 in which:
  $R^2$ is
   1) a hydrogen atom,
   2) $(C_1-C_5)$-alkyl, or
   3) phenyl.

3. A compound of the formula I or II as claimed in claim 1, in which
$R^1$ is
 a) a hydrogen atom,
 b) a covalent bond,
 c) glucose, or
 d) polyethylene glycol having a molecular weight of from 100 to 3000 g/mol,
X is
 a) a hydrogen atom, or
 b) $-OR^2$,
 where $R^2$ is tertiary butyl.

4. A compound of the formula I or II as claimed in claim 1, in which $R^1$ is a polyethylene residue having a molecular weight of 1500 g/mol.

5. A process for preparing the compounds as claimed in claim 1, wherein an amine derivative of the formula IIIa or IIIb is reacted with hirudin in the presence of protease.

6. The process as claimed in claim 5, wherein the protease is selected from the group consisting of chymotrypsin, trypsin, and a trypsin-like enzyme.

7. The process as claimed in claim 5, wherein the protease is lysyl endopeptidase.

8. A compound of the formula I or II as claimed in claim 1, in which $R^1$ is a monosaccharide selected from the group consisting of glucose, fructose, mannose, galactose, ribose, ribulose and xylose.

9. A compound of the formula I or II as claimed in claim 1, in which $R^1$ is a polysaccharide containing from 2 to 10 monosaccharides selected from the group consisting of glucose, fructose, mannose, galactose, ribose, ribulose and xylose.

10. A compound of the formula I or II,

A0-A1-A2-(hirudin 3–36)-(Y), (hirudin 37–65)   (I),

A0-A1-A2-(hirudin 3–63)-(Y)   (II), wherein:
A1 is an amino acid residue,
A2 is an amino acid residue,
A0 is an amino acid residue or a hydrogen atom,
Y is an amine derivative of the formula IIIa:

NH—R—X   (IIIa), where:
R is
a) $(C_1-C_{10})$-alkyl, branched or straight-chain, or
b) $(C_1-C10)$-alkyl, branched or straight-chain, substituted once or more than once, independently of each other, by
 1) phenyl
 2) indolyl,
 3) imidazolyl, or
 4) phenyl, substituted once or more than once by hydroxyl,
c) phenyl, or
d) naphthyl, X is
a) a hydrogen atom,
b) $-OR^2$,
c) $-SR^2$, d) —NHR$^2$, e) —COOR$^2$, or f) A, where:

A is a peptide having from 2 to 5 amino acid residues selected from the group consisting of Thr and Arg, R$^2$ is 1) a hydrogen atom,
2) (C$_1$–C$_{10}$)-alkyl, branched or straight-chain,
3) (C$_1$–C10)-alkyl, branched or straight-chain, substituted once or more than once, by 3.1 phenyl,
    3.2 indolyl,
    3.3 imidazolyl, or
    3.4 phenyl, substituted once or more than once by hydroxyl,
4) phenyl, or
5) naphthyl.

11. A compound of the formula I or II as claimed in claim 10, in which:

R is ethyl, substituted by 1) phenyl,
2) indolyl,
3) imidazolyl, or
4) 4-hydroxyphenyl, X is a) a hydrogen atom,
b) —OR$^2$,
c) —NHR$^2$, or
d) —COOR$^2$, in which:

R$^2$ is 1) a hydrogen atom,
2) (C$_1$–C$_5$)-alkyl, or
3) phenyl.

12. A compound of the formula I or II as claimed in claim 10 in which:

X is a) a hydrogen atom, or
b) —OR$^2$, where R$^2$ is tertiary butyl.

13. A pharmaceutical composition containing an effective amount of a compound of the formula I or II as claimed in claim 1.

14. A process for preparing a pharmaceutical composition having an anti-coagulatory effect which comprises incorporating in said pharmaceutical composition an effective amount of a compound of the formula I or II as claimed in claim 1.

15. A method which comprises the transdermal administration of the pharmaceutical composition as claimed in claim 13.

16. The method of claim 15, wherein the transdermal administration is by iontophoresis.

* * * * *

UNITED STATES PATENT AND TRADEMARK OFFICE
CERTIFICATE OF CORRECTION

PATENT NO. : 5,674,838
DATED : October 07, 1997
INVENTOR(S) : Rainer OBERMEIER et al.

It is certified that error appears in the above-indentified patent and that said Letters Patent is hereby corrected as shown below:

Claim 1, column 15, line 1, before "a peptide", delete "a)".

Claim 1, column 15, line 20, after "monosaccharide", insert --,--, and delete "xylose,".

Claim 2, column 15, line 55, "4-hydroxphenyl" should read --4-hydroxyphenyl--.

Claim 2, column 15, line 60, before "hydrogen", insert --a--.

Claim 5, column 16, line 21, before "protease", insert --a--.

Claim 10, column 16, line 53, "$(C_1-C10)$" should read --$(C_1-C_{10})$--.

UNITED STATES PATENT AND TRADEMARK OFFICE
CERTIFICATE OF CORRECTION

PATENT NO. : 5,674,838
DATED : October 07, 1997
INVENTOR(S) : Rainer OBERMEIER et al.

It is certified that error appears in the above-identified patent and that said Letters Patent is hereby corrected as shown below:

Claim 10, column 17, line 10, "$(C_1-C10)$" should read --$(C_1-C_{10})$--.

Claim 10, column 17, line 11, after "by", insert a line break.

Signed and Sealed this

Twenty-seventh Day of October, 1998

BRUCE LEHMAN

*Attest:*

*Attesting Officer*          *Commissioner of Patents and Trademarks*